United States Patent [19]

Chang

[11] Patent Number: 4,917,671
[45] Date of Patent: Apr. 17, 1990

[54] FLASH PLUG FOR I.V. CATHETERS

[75] Inventor: Joseph J. Chang, Tampa, Fla.

[73] Assignee: Critikon, Inc., Tampa, Fla.

[21] Appl. No.: 221,579

[22] Filed: Jul. 20, 1988

[51] Int. Cl.[4] .............................................. A61M 5/00
[52] U.S. Cl. ................................. 604/168; 604/256; 604/900
[58] Field of Search ................ 604/168, 900, 126, 256

[56] References Cited

U.S. PATENT DOCUMENTS

| | | |
|---|---|---|
| 3,859,998 | 1/1975 | Thomas et al. . |
| 4,193,399 | 3/1980 | Robinson . |
| 4,193,400 | 3/1980 | Loveless et al. . |
| 4,207,870 | 6/1980 | Eldridge ............................. 604/168 |
| 4,365,630 | 12/1982 | McFarlane . |

Primary Examiner—Stephen C. Pellegrino
Attorney, Agent, or Firm—W. Brinton Yorks, Jr.

[57] ABSTRACT

A flash plug for an I.V. catheter is formed of a body of polymeric material, and has a narrow distal end for insertion within a catheter flash chamber and a larger proximal end which extends from the flash chamber. The flash plug has an aperture extending through it from the distal to the proximal end. An insert of a porous material is located within the aperture, and is capable of passing air and blocking the flow of blood. The catheter body is compatible with flash chamber material so as to remain securely located within the flash chamber and provides protection for the insert. The aperture diameter is sized to retain the porous insert securely within the flash plug body.

11 Claims, 2 Drawing Sheets

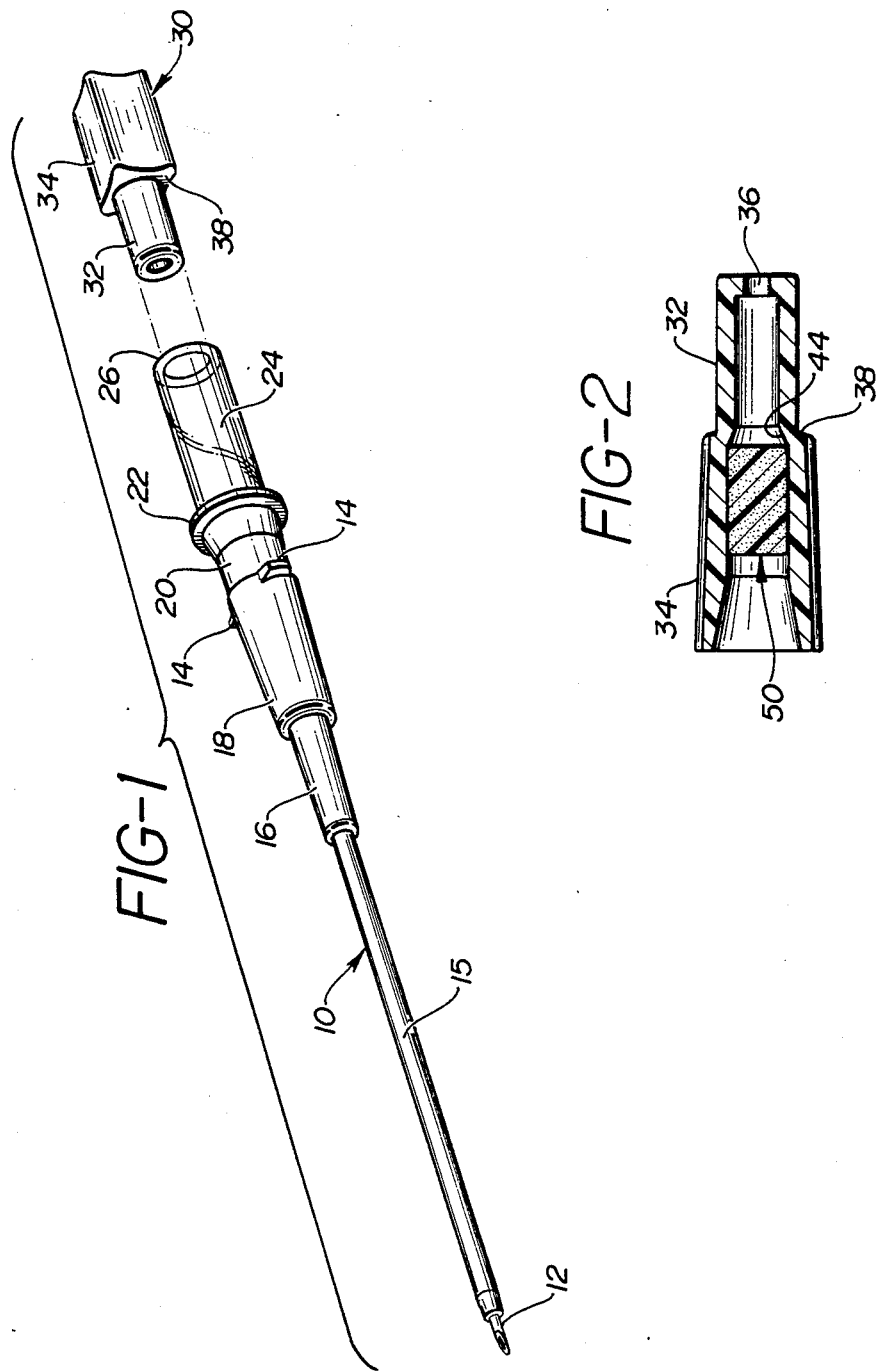

FLASH PLUG FOR I.V. CATHETERS

This invention relates to intravenous catheter assemblies for the administration of fluids to patients and, in particular, to means for venting air to enable blood to flow from a blood vessel during a venipuncture procedure into a blood-detecting chamber in the catheter assembly.

During the placement of a needle or flexible plastic catheter into a vein or other body member, it is desirable to determine whether or not the tip of the needle or catheter is properly situated within the vessel. Because the introduction of the assembly into the vein is normally accomplished by the use of a rigid metallic needle, it is impossible to detect the presence of blood in the needle and, likewise, the presence of the needle tip in the vein. Introducer needles are normally equipped with a hub and some prior art devices have equipped the hub portion of the needle with transparent flash chambers into which the blood may flow to indicate that the needle point is properly placed. The flash chamber in turn is conventionally sealed at the rear by a vented membrane or flash plug which serves two purposes: to rapidly vent air from the flash chamber so that it will quickly fill with blood when the needle and catheter are properly situated, and to prevent leakage of blood from the filled flash chamber.

These two functions of a flash plug are inherently contradictory. On the one hand the flash plug should readily permit the flow of air from the needle and flash chamber. But on the other hand, the flash plug should completely seal the flash chamber so that there is no blood leakage.

The prior art contains several approaches directed toward meeting these conflicting requirements. U.S. Pat. No. 3,859,998 shows a flash plug with a slitted diaphragm. The slit in the diaphragm will permit the flow of air out of the flash chamber, but will not readily pass blood by reason of the viscosity of the blood and surface friction. In some circumstances, however, the slit does not completely prevent leakage. Another flash plug with a slitted diaphragm is shown in U.S. Pat. No. 4,193,400. In the flash plug of that paten,, the portion of the flash plug which extends into the flash chamber contains three slits.

A second approach to a venting flash plug is shown in U.S. Pat. No. 4,365,998. The catheter in that patent contains a flash chamber with dividers forming a maze-like blood flow path through the chamber. The flash chamber includes the necessary venting port at the rear of the chamber, however, so that, while the maze may deter the passage of blood through the chamber, it will still ultimately arrive at the venting port and leak out of the catheter.

Another approach to a venting flash plug is shown in U.S. Pat. No. 4,193,399. In that patent the flash plug is made of a porous polymeric material which passes air, but has a pore size small enough to oppose blood flow through the material. The material used in the '399 patent is an ultra-high molecular weight polyethylene (UHMWPE), available commercially under the trade name "POREX" from the Porex Materials Corporation.

While the UHMWPE type material acceptably meets the above two requirements for a flash plug, the present inventor has found that it also presents several limitations. The UHMWPE plug is made of a sintered polyethylene material, and accordingly is rather brittle. It has been found that the plug can fracture when it is accidentally bent or dropped. A flash plug with better structural characteristics would be more desirable. Additionally, the UHMWPE material is characterized by a high modulus and low elastic limit. Consequently when it is compressed as it is inserted into the flash chamber, it will not decompress and spring back to its full original diameter. Furthermore, the modulus differential between the high modulus plug and a flash chamber of low density material, such as low density polyethylene, provides the flash plug with low creep resistance when inserted into the flash chamber. This combination of material characteristics causes the UHMWPE plug to exhibit low retention forces in the flash chamber. Consequently, the flash plug will often vibrate out of the flash chamber during transportation, presenting the user with the impression that the catheter has not been fully assembled or has been tampered with. It is desirable for a flash plug not to become easilY dislodged during transit to the user. It is further desirable for a flash plug to be capable of inexpensive manufacture in quantity, and to be made by relatively simple processing techniques.

In accordance with the principles of the present invention, a flash plug is provided for the flash chamber of an I.V. catheter. The flash plug comprises a generally cylindrical body with a shoulder demarcating the diametric transition between the smaller distal end of the plug which engages the flash chamber and the larger proximal end extending from the flash chamber. The body is formed of a material compatible with the flash chamber material for secure retention therein. The flash plug body includes a passageWay extending therethrough which contains an insert of a porous material. The flash plug is thus simple and economic to manufacture, and provides the advantages of air permeability and leakage prevention of the UHMWPE plug, with secure retention within the flash chamber. In a preferred embodiment, the flash plug passageway is sized to an internal diameter slightly smaller than that of the porous insert. The passageway may also be tapered to a smaller diameter at the distal end of the flash plug. The insert is retained in place in the passageway by a gate projecting from the interior wall of the passageway proximal the intended location of the insert in the passageway.

IN THE DRAWINGS

FIG. 1 is a perspective view of an I.V. catheter assembly constructed in accordance with the principles of the present invention;

FIG. 2 is a cross-sectional view of the flash plug of FIG. 1, including a rod-like insert of porous material;

Figure 3:
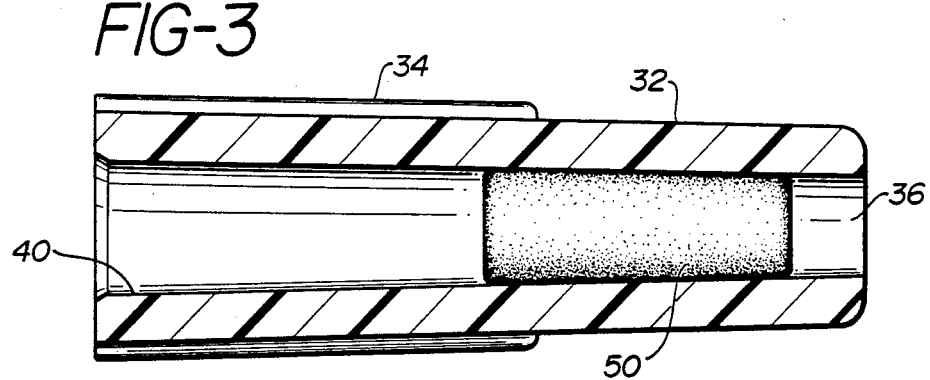
FIG. 3 is a cross-sectional view of a flash plug constructed in accordance with the principles of the present invention.

Referring first to FIG. 1, an I.V. catheter constructed in accordance with the principles of the present invention is shown. The catheter 10 comprises a tube 15 made of fluorinated ethylene propylene or polyurethane material. The tube 15 is tapered at its distal end where it may easily slide into an opening in the patient's body formed by a hollow needle 12. The catheter tube 15 is concentrically affixed by mechanical or adhesive means to a catheter hub 16, 18. The dual diameter hub terminates at its proximal end in a tab or fitting 14, suitable for attaching the catheter hub to a tubing set which administers a source of intravenous fluid.

The catheter 10 is engaged by the hollow needle 12, which is affixed to its own hub 20. The needle hub 20 is hollow and includes a proximally located flange 22. Molded to the flange is a hollow flash chamber 24, which is made of a transparent or translucent polymer such as polypropylene or polycarbonate. The proximal end of the needle terminates in the hub 20, just short of the flash chamber. In a preferred embodiment the interior diameter of the hub at the proximal end of the needle 12 is approximately the same as the interior diameter of the flash chamber 24. The flash chamber 24 terminates at its proximal end 26.

Inserted into the flash chamber 24 (but shown separated just prior to insertion in FIG. 1) is a flash plug 30. The flash plug 30 is made of a polymeric material compatible with the material of the flash chamber such that the flash plug will frictionally remain in place when inserted into the flash chamber. In a constructed embodiment the flash plug body is formed of low density polyethylene (LDPE). The flash plug body comprises a smaller diameter distal end 32 sized for a frictional fit in the flash chamber 24, and a somewhat square proximal end 34 with convex sides, which enables an assembler to easily grasp and insert the flash plug into the flash chamber. At the jointure of the distal and proximal portions of the flash plug 30 is a shoulder 38 which meets the proximal end 26 of the flash chamber 24 when the flash plug 30 is fully inserted into the flash chamber. The flash plug 30 is hollow with an aperture 36 extending completely through the flash plug body. The distal opening of the aperture 36 is visible in FIG. 1.

The flash plug 30 of FIG. 1 is shown in cross-section in FIG. 2. This drawing shows the several interior diameters of the aperture 36. Located in the larger interior diameter of the proximal end of the flash plug is a cylindrical insert 50 of porous material. In the preferred embodiment the insert 50 is made of ultra-high molecular weight polyethylene (UHMWPE). At the distal end of the flash plug the aperture 36 is narrowed to prevent the porous insert from escaping from the aperture and entering the flash chamber. The interior of the narrow diameter portion 32 of the flash plug is also of a smaller diameter than the outer diameter of the porous insert 50 to prevent passage of the insert beyond the larger diameter portion 34 of the plug. The transition in interior diameter of the aperture 36 is indicated at 44. It may be appreciated that even a very small interior diameter within the distal portion 32 will be sufficient, since even a very small passageway will accommodate a substantial air flow from the flash chamber.

A second embodiment of the flash plug 30 of the present invention is shown in FIG. 3. In this embodiment the aperture 36 is continuous tapered from a larger diameter at the proximal end of the flash plug to a smaller diameter at the distal end. The porous insert 50 slides into the aperture from the proximal end, and will slide through the aperture until it is seated by a tight interference fit toward the distal end (toward the right in the drawing). The flash plug of FIG. 3 may be easily molded in a simple mold that will readily maintain the aperture tolerance necessary for the secure interference fit. The porous insert 50 will remain tightly in place in the flash plug due to the relatively significant thickness of the walls of the flash plug, especially as compared with the thinner wall of the flash camber. In addition, the porous insert is retained in the flash plug by the compressive forces of both the flash plug walls and the engaging wall of the flash chamber when the distal portion 32 is engaged within the flash chamber. The LDPE flash plug itself remains secure within the polypropylene or polycarbonate flash chamber.

Figure 4:
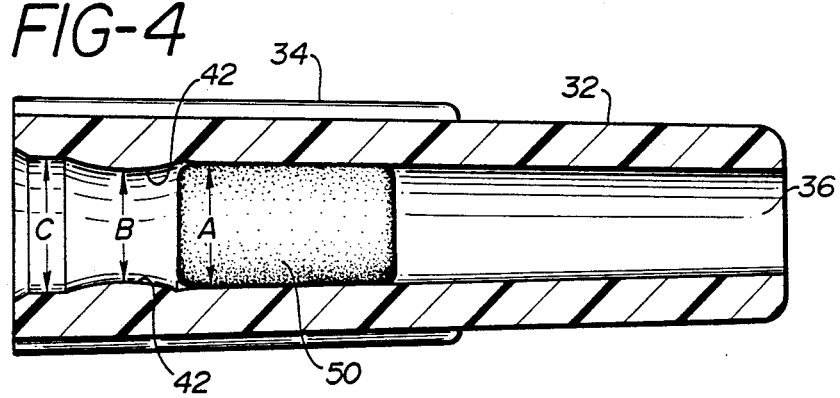
FIG. 4 is a preferred embodiment of a flash plug of the present invention with the porous insert retained by a minimum interference fit.
Figure 5:
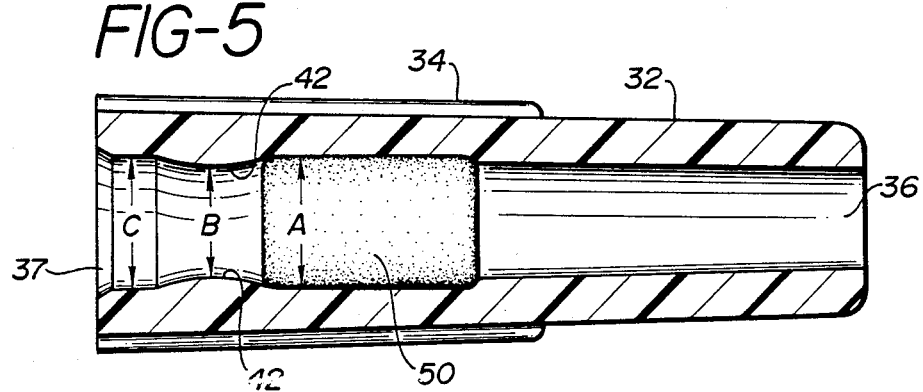
FIG. 5 is a second preferred embodiment of a flash plug of the present invention with the porous insert retained by a maximum interference fit.

When it is anticipated that the catheter will experience significant vibration and shock during transport, it may additionally be desirable to form a gate within the aperture 36 to prevent the porous insert from vibrating out of the proximal end of the flash plug. FIGS. 4 and 5 are cross-sectional views of flash plug 30 with a gate or projection 42 formed proximal the porous insert 50. FIG. 4 shows a flash plug in which the porous insert is held in a minimal interference fit, and FIG. 5 illustrates a maximal interference fit. In both FIGURES the flash plug body has a length of approximately 0.6 inches, and the length of the insert is approximately 0.2 inches.

In the embodiment of FIG. 4, the cylindrical insert 50 has an outer diameter of approximately 0.136 inches as indicated at "A". At the peak of the concentric gate 42 the aperture has an inner diameter of approximately 0.133 inches as indicated at "B". Proximal the gate 42 the aperture 36 has an inner diameter of 0.148 inches as indicated at "C". From the gate to the distal end of the flash plug the aperture 36 is continually tapered to a smaller interior diameter to prevent migration of the porous insert out the distal end of the flash plug. It has been found that the gently rounded gate 42 will permit the porous insert to slide over the gate when inserted from the proximal end of the flash plug, and the gate is sufficiently elastic to decompress to its original shape after passage of the insert, a characteristic of the LDPE material.

In the maximal interference fit of FIG. 5, the porous insert 50 has an outer diameter of approximately 0.146 inches as indicated at "A". The interior diameter at the peak "B" of the gate 42 is approximately 0.127 inches. Proximal the gate the aperture 36 has an interior diameter of approximately 0.142 inches as indicated at "C". Again the aperture tapers to an even smaller diameter at the distal end of the flash plug. It may be appreciated that with these interior dimensions the porous insert 50 must be forced through the smaller diameters of both C and B, and for that reason the proximal end of the aperture is flared at 37 for insertion of the insert 50.

The embodiments of FIGS. 4 and 5 satisfy all of the criteria of a good I.V. catheter flash plug. These flash plugs prevent the porous insert of UHMWPE material from vibrating out of the flash plug aperture, either distally due to the narrow distal diameter or proximally due to the gate 42. The embodiment of FIG. 3 has been found to also be satisfactory for this purpose, since the porous insert is located in the distal end of the flash plug, a substantial distance from the proximal end. All of the illustrated embodiments have been found during in-vitro testing to exhibit high air venting capability, permitting the flash chamber to vent and fill with blood in less than one second for needle gauges of 22 and less; for needle gauges of 24 and greater the flashback is substantially instantaneous. It has been found that all of the embodiments prevent blood leakage through the plug during and after venous or arterial insertion. The flash plugs do not become loose in the flash chamber due to the compatibility of the lower density materials of the flash plug body and the flash chamber, and porous insert will not break or fracture since it is protected by the plug body. The flash plug bodies illustrated are easy and inexpensive to mold in quantities while holding the necessary tolerances, and are easy to assemble.

A further requirement for a flash plug is that the flash plug and catheter must be susceptible of complete and thorough sterilization. To determine whether the flash plugs of the present invention may be readily sterilized, a number of samples were tested using inserts of different porosity in a gas sterilization process. The insert samples were formed of ultra high molecular weight polyethylene and high density polyethylene. The tested inserts each had an outside diameter of 0.115 inches and a length of 0.2 inches, and were inserted in flash plugs constructed as shown in FIG. 3. All samples were found to exhibit air flow rates in excess of that of the control samples, which were the slitted flash plugs shown in the aforementioned U.S. Pat. No. 3,859,998 for a 22 gauge catheter. The results of this testing are summarized in the following table:

| AIR PRESSURE | AIR FLOW RATE, SCCM | | | |
|---|---|---|---|---|
| | 22.7 MICRONS 44% POROSITY | 25-55 MICRONS +30% POROSITY | 35 MICRONS 42.4% POROSITY | CONTROL |
| 10 mmHg | 15.5 avg. | 19.5 avg. | 27.5 avg | 7.5 avg. |
| " | 23.0 high | 25.0 high | 35.5 high | 14.5 high |
| " | 8.0 low | 12.0 low | 20.0 low | 4.0 low |
| 20 mmHg | 34.0 avg. | 35.0 avg. | 47.5 avg. | 12.5 avg. |
| " | 44.5 high | 46.0 high | 62.5 high | 17.0 high |
| " | 22.0 low | 23.0 low | 36.5 low | 7.5 low |

What is claimed is:

1. A flash plug for an I.V. catheter comprising:
   a flash plug body formed of a polymeric material, and including a relatively narrow outside diameter distal end for engaging a catheter flash chamber and a relatively larger outside diameter proximal end for extending from said flash chamber, said narrow and larger outside diameter portions being separated by a shoulder for engaging the proximal end of said flash chamber, said flash plug body including an aperture extending through said distal end proximal portions of said body, said aperture exhibiting a relatively smaller interior diameter within said distal end than the interior diameter of said aperture within said proximal end; and
   an insert formed of a porous material and located within said aperture intermediate the terminal ends of said aperture to retain blood within said flash chamber and within said aperture distal said insert, said insert being sized so as to be insertable through said proximal end of said aperture and incapable of passage through said relatively smaller diameter distal portion of said aperture.

2. The flash plug of claim 1, wherein said porous insert is formed of an ultra-high molecular weight polyethylene material.

3. The flash plug of claim 2, wherein the average pore size of the pores of said porous insert is within the range of 22.7 to 55 microns, whereby said porous insert exhibits a porosity within the range of 30% to 44%.

4. The flash plug of claim 2, wherein said flash plug body is formed of low density polyethylene.

5. The flash plug of claim 4, wherein said flash plug is suitable for secure retention in a catheter flash formed of polypropylene or polycarbonate material.

6. The flash plug of claim 2, wherein said aperture is narrowed at the distal end of said flash plug to prevent passage of said porous insert out said distal end.

7. The flash plug of claim 1, wherein the interior diameter of said aperture undergoes a transition from a relatively larger constant diameter at said proximal end of said body to a relatively smaller constant diameter at said distal end,
   wherein said diameter of said aperture at said distal end of said body is less than the diameter of said porous insert.

8. A flash plug for an I.V. catheter comprising:
   a flash plug body formed of a polymeric material, and including a relatively narrow diameter distal end for engaging a catheter flash chamber and a relatively larger diameter proximal end for extending from said flash chamber, said narrow and larger diameter portions being separated by a shoulder for engaging the proximal end of said flash chamber, said flash plug body including an aperture extending through said distal and proximal portions of said body; and
   an insert formed of a porous material and located within said aperture,
   wherein the interior diameter of said aperture is tapered from a relatively larger diameter at said proximal end of said body to a relatively smaller diameter at said distal end,
   wherein said diameter at said distal end of said body is less than the diameter of said porous insert, and
   wherein said interior diameter of said aperture is tapered such that said porous insert becomes securely seated when inserted into said flash plug body from said proximal end of said body to a position which is substantially within said narrow diameter portion of said body.

9. A flash plug for an I.V. catheter comprising:
   a flash plug body formed of a polymeric material, and including a relatively narrow diameter distal end for engaging a catheter flash chamber and a relatively larger diameter proximal end for extending from said flash chamber, said narrow and larger diameter portions being separated by a shoulder for engaging the proximal end of said flash chamber, said flash plug body including an aperture extending through said distal and proximal portions of said body; and
   an insert formed of a porous material and located within said aperture.
   wherein said aperture of said body further includes a gate means formed within said aperture at a location proximal the intended position of said insert within said aperture for inhibiting passage of said insert out said proximal end of said body.

10. The flash plug of claim 9, wherein said gate means is formed in said aperture inside said larger diameter portion of said body, the interior diameter of said aperture at said distal end of said body is less than the outer diameter of said porous insert, and wherein said interior diameter of said aperture proximal said gate means is larger than the outer diameter of said porous insert,
whereby said porous insert is retained within said aperture in a minimal interference fit.

11. The flash plug of claim 9, wherein said gate means is formed in said aperture inside said larger diameter portion of said body, the interior diameter of said aperture at said distal end of said body is less than the outer diameter of said porous insert, and wherein said interior diameter of said aperture proximal said gate means is less than the outer diameter of said porous insert,
whereby said porous insert is retained within said aperture in a maximal interference fit.

* * * * *